US009574990B2

(12) United States Patent
Mourey et al.

(10) Patent No.: US 9,574,990 B2
(45) Date of Patent: Feb. 21, 2017

(54) SERS STRUCTURES WITH NANOPOROUS MATERIALS (75) Inventors: Devin Alexander Mourey, Albany, OR (US); Vladek Kasperchik, Corvallis, OR (US); James William Stasiak, Lebanon, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 116 days.

(21) Appl. No.: 14/377,708

(22) PCT Filed: Feb. 28, 2012

(86) PCT No.: PCT/US2012/026902
§ 371 (c)(1),
(2), (4) Date: Aug. 8, 2014

(87) PCT Pub. No.: WO2013/130043
PCT Pub. Date: Sep. 6, 2013

(65) Prior Publication Data
US 2015/0316465 A1 Nov. 5, 2015

(51) Int. Cl.
*G01N 21/65* (2006.01)
*G01N 21/01* (2006.01)
(52) U.S. Cl.
CPC ............ *G01N 21/01* (2013.01); *G01N 21/658* (2013.01); *G01N 2201/02* (2013.01); *G01N 2201/068* (2013.01)
(58) Field of Classification Search
CPC .................................................. G01N 21/658
See application file for complete search history.

(56) References Cited

U.S. PATENT DOCUMENTS

| 6,756,795 | B2 | 6/2004 | Hunt et al. |
| 6,970,239 | B2 | 11/2005 | Chan et al. |
| 8,767,202 | B2 * | 7/2014 | Schmidt ............... G01N 21/658 356/301 |
| 9,134,247 | B2 * | 9/2015 | Sengupta ............. G01N 21/658 |
| 2003/0039808 | A1 * | 2/2003 | Ichinose ............... B41M 5/502 428/195.1 |
| 2008/0024776 | A1 | 1/2008 | Bratkovski |
| 2008/0174775 | A1 | 7/2008 | Moskovits et al. |

(Continued)

FOREIGN PATENT DOCUMENTS

WO   WO-2011133143   10/2011

OTHER PUBLICATIONS

Sun, Yinghui, et al. "Highly sensitive surface-enhanced Raman scattering substrate made from superaligned carbon nanotubes." Nano letters 10.5 (2010): 1747-1753.*

(Continued)

*Primary Examiner* — Kara E Geisel
*Assistant Examiner* — Shawn Decenzo
(74) *Attorney, Agent, or Firm* — Brooks, Cameron & Huebsch, PLLC (57) ABSTRACT The present disclosure describes a surface enhanced Raman spectroscopy (SERS) apparatus and methods of forming and using the SERS apparatus. An example of a SERS apparatus includes a nanoporous material on an upper surface of a substrate, a plurality of SERS-active structures on an upper surface of the nanoporous material, and a Raman-active material on a surface of each of SERS-active structures.

21 Claims, 5 Drawing Sheets (56) References Cited

U.S. PATENT DOCUMENTS

| | | | |
|---|---|---|---|
| 2008/0248235 A1* | 10/2008 | Feng | B32B 38/10 |
| | | | 428/113 |
| 2009/0122310 A1* | 5/2009 | Zhang | B82Y 15/00 |
| | | | 356/301 |
| 2011/0003174 A1* | 1/2011 | Hikata | B82Y 10/00 |
| | | | 428/688 |
| 2011/0014300 A1 | 1/2011 | Muthusamy et al. | |
| 2011/0045230 A1 | 2/2011 | Habib et al. | |
| 2011/0128535 A1* | 6/2011 | Baker | C03B 32/00 |
| | | | 356/301 |
| 2014/0347661 A1* | 11/2014 | Kim | G01N 21/658 |
| | | | 356/301 |

OTHER PUBLICATIONS

Sun, Yinghui, et al. "Supporting Information for: Highly sensitive surface-enhanced Raman scattering substrate made from superaligned carbon nanotubes." Nano letters 10.5 (2010): 1747-1753.*

Lee, Wonjoo, et al. "Self-Assembled SERS Substrates with Tunable Surface Plasmon Resonances." Advanced Functional Materials 21.18 (2011): 3424-3429.*

Williamson, et al.;Porous GAN as a Template to Produce Surface-enhanced Raman Scattering-active Surfaces; Aug. 25, 2005, pp. 20186-20191, vol. 109, Issue 43.

* cited by examiner

SERS STRUCTURES WITH NANOPOROUS MATERIALS

BACKGROUND

Molecules can be identified using Raman spectroscopy. When molecules are placed on particular surfaces an enhanced Raman signal is produced such that a particular signal may be markedly increased, which contributes to surface enhanced Raman spectroscopy (SERS). The increased signal can include a spectrum that is uniquely identifiable to a particular molecule.

DETAILED DESCRIPTION

As Raman enhancement improves, the ability to detect particular molecules becomes increasingly possible. There are a wide range of applications in both the chemical and biomolecular areas that benefit from SERS ability to detect particular molecules. However, as SERS technology increases in both complexity and number of applications, so too does the challenge of reproducibility and signal reliability.

As the level of enhancement increases, effects of errors (e.g., improper sample production, unintended surface variations, and others resulting in non-uniform Raman signal production) also are amplified. These errors may become notable when trying to reliably reproduce signals. Usability of Raman signal enhancement may depend upon on an ability to create an increased Raman signal that has both high intensity and high reproducibility.

To realize the goal of such a SERS apparatus, individual SERS-active structures can be integrated into a larger array of SERS-active structures. A potential difficulty is that as the number of SERS-active structures increases, uniform formation of the SERS-active structures and uniform application of a material of interest present in a solution being analyzed may become increasingly difficult. Increasing the number of SERS-active structures and the complexity of their orientation may make reliable fabrication and reproducible implementation of the SERS apparatus difficult. Accordingly, maintaining reliable and consistent surface topology is important in improving the intensity and reproducibility of the enhancement of the Raman signal.

Nanoporous materials used in conjunction with SERS-active structures, as described in the present disclosure, can contribute to high signal intensity and reproducibility. Further, nanoporous materials can be incorporated directly onto a substrate of a given array because layers of nanoporous material can be thin, among other considerations. Nanoporous material may be readily fabricated (e.g., by single-pass curtain coating techniques), as described herein. As described herein, both the nanoporous material and the SER-active structures can contribute to controlling the surface topology of the SERS apparatus, resulting in improved presentation of particular molecules for spectroscopy, as disclosed herein.

Figure 1:
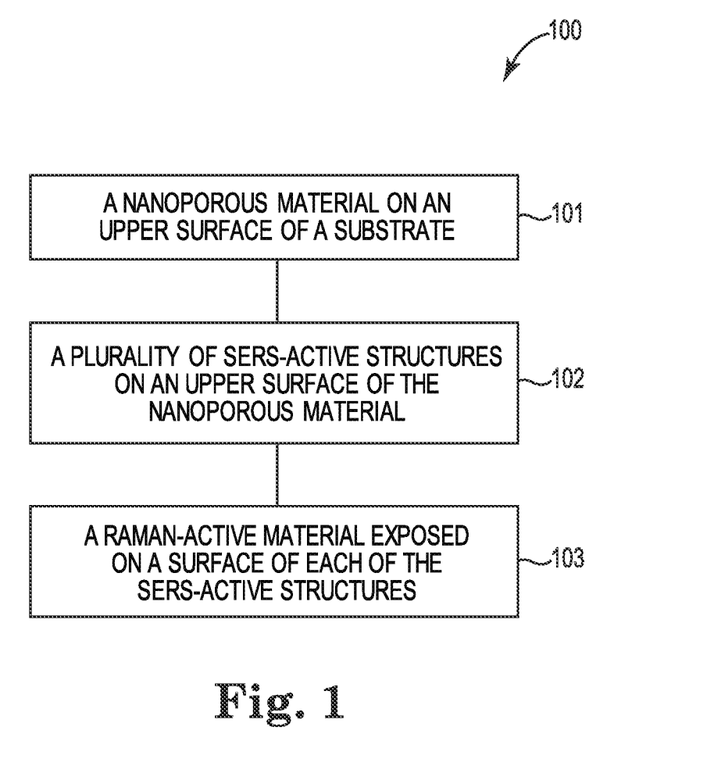
FIG. 1 is a block diagram illustrating an example of a method of forming a portion of a SERS apparatus formed according to the present disclosure

FIG. 1 is a block diagram illustrating an example of a method of forming a portion of a SERS apparatus formed according to the present disclosure. In accordance with the SERS apparatus described herein, there is nanoporous material on an upper surface of a substrate, as shown in block 101. As shown in block 102, there is a plurality of SERS-active structures on an upper surface of the nanoporous material. As shown in block box 103, the apparatus includes a Raman-active material exposed on a surface of each of the SERS-active structures. The plurality of SERS-active structures, with Raman-active material exposed thereon can provide multiple locations for binding of material of interest, thereby enabling a surface enhanced Raman signal.

Figure 2:
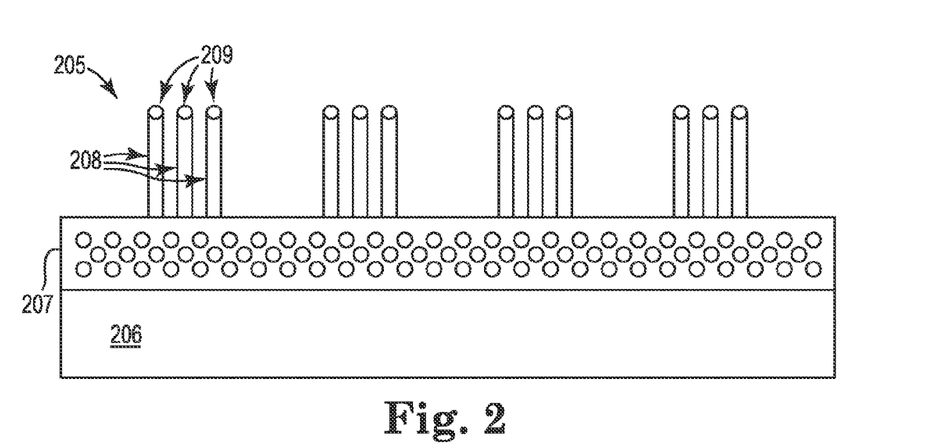
FIG. 2 illustrates an example of a side-view schematic of a portion of a SERS apparatus according to the present disclosure.

FIG. 2 illustrates an example of a side-view schematic of a portion of a SERS apparatus 205 according to the present disclosure. The example of the SERS apparatus 205 includes a substrate 206, a nanoporous material 207, and a plurality of SERS-active structures 208, each having an at least partially exposed Raman-active (e.g., a metal-containing material) material 209. FIG. 2 illustrates, by way of example, the SERS-apparatus 205 where the plurality of SERS-active structures 208 are nanopillars. However, the present disclosure is not limited to nanopillars. That is, the shape and orientation of the plurality of SERS-active structures 208 can include any shape and orientation that is conducive to the reliable production of an enhanced Raman signal. The plurality of SERS-active structures can, in various examples, include arrays of nanoparticles, nanopillars and/or combinations thereof, among other suitable SERS-active structures.

In the detailed description of the present disclosure, reference is made to the accompanying drawings that form a part hereof and in which is shown by way of illustration examples of how the disclosure may be practiced. These examples are described in sufficient detail to enable those of ordinary skill in the art to practice the embodiments of this disclosure. It is to be understood that other examples may be utilized and that material variations and/or structural changes may be made without departing from the scope of the present disclosure. Further, where appropriate, as used herein, "for example" and "by way of example" should each be understood as an abbreviation for "by way of example and not by way of limitation".

The figures herein follow a numbering convention in which the first digit or digits correspond to the drawing figure number and the remaining digits identify an element or component in the drawing. Similar elements or components between different figures may be identified by the use of similar digits. For example, 104 may reference element "104" in FIG. 1, and a similar element may be referenced as "204" in FIG. 2. Elements shown in the various figures herein can be added, exchanged, and/or eliminated so as to provide a number of additional examples of the present disclosure. In addition, the proportion and the relative scale of the elements provided in the figures are intended to illustrate the examples of the present disclosure and should not be taken in a limiting sense.

Unless otherwise indicated, all numbers expressing ranges and dimensions, and so forth, used in the specification and claims are to be understood as being modified in all instances by the terms "substantially" or "about". Accordingly, unless indicated to the contrary, the numerical parameters set forth in the following specification and attached claims are approximations that may vary depending upon the desired properties sought to be obtained.

An example of a substrate as described herein is substrate 206 as indicated in FIG. 2. The substrate 206 can provide mechanical structural support and durability to the upper layers, for example, because nanoporous material 207 and SERS-active structures 208 may lack mechanical rigidity and durability. The nanoporous material 207 forms one or more layers on the substrate 206, as described herein. In some examples, the nanoporous material 207 can have a thickness in a range of from substantially 2 microns ($\mu$m) to substantially 50 ($\mu$m).

In some examples, the nanoporous material 207 can have at least two layers, each having different materials and/or different sized particles to provide the desired properties for the SERS apparatus 205. Further, in some examples, the nanoporous material 207 can include at least two layers, each having differing median pore diameter, as described herein.

The substrate 206, which supports the nanoporous material 207, may take the form of a sheet, a web, or a three-dimensional object of various shapes, as described herein. The substrate 206 can be of any type and size. The substrate 206 can be any material that provides mechanical support to the above mentioned components of the SERS apparatus 205. Consistent with the present disclosure, a variety of substrate materials may be used, which provide a range of physical characteristics such as mechanical strength, flexibility, and resilience to heat and/or pressure. In some examples, the substrate 206 can be a flexible film or a rigid paper substrate. As non-limiting examples, the substrate 206 may be selected from cellulosic or synthetic paper (coated or uncoated), cardboard, polymeric film (e.g., a plastic sheet of polyethylene terephthalate (PET), polycarbonate, polyethylene, polypropylene), fabric, cloth, and other textiles. In some examples, the substrate 206 may be a single material plastic film made from PET, polyimide or another suitable polymer film with adequate mechanical properties. In some examples, the substrate 206 can include any substrate that is suitable for use in digital color imaging devices, such as electrophotographic and/or inkjet imaging devices, including, but not limited to, resin coated papers (so-called photobase papers), other coated or uncoated papers, overhead projector plastics, fabrics, plastic film of any kind, and the like.

The substrate 206 can include porous and non-porous surfaces. In some other examples, the substrate 206 is paper (non-limitative examples of which include plain copy paper or papers having recycled fibers therein) or photopaper (non-limitative examples of which include polyethylene or polypropylene extruded on one or both sides of paper), and/or combinations thereof.

In some examples, the substrate 206 is a photobase. Photobase is a supporting base substrate used in coated photographic paper, which includes a paper base extruded one or both sides with polymers (e.g., with polyethylene and/or polypropylene, where coat weight of the extruded polymer layers is from about 5 to about 45 grams per square meter (g/m$^2$)). Photobase support can include a photobase material including a paper extruded with a layer of polyethylene on both sides. In this regard, the photobase support can be an opaque water-resistant material exhibiting qualities of silver halide paper. In some examples, the photobase support can include a polyethylene layer having a thickness of about 10 to about 24 g/m$^2$. The photobase support can also be made of transparent or opaque photographic material. In some examples, the substrate 206 can have a thickness along substantially the entire length of the substrate 206 ranging between about 0.025 mm to about 0.5 mm.

In some examples, the nanoporous material 207 is patterned for directing solution containing a material of interest to predetermined areas of the nanoporous material 207 and/or substrate 206. Through techniques such as photolithography or shadow mask, a material such as a photoresist can be used to seal or expose portions of the nanoporous layer therein creating fluidic channels on the substrate. As such, a material of interest in the solution and/or the solution itself can be steered to specific portions of the exposed nanoporous material 207 and/or substrate 206.

As described in the present disclosure, a SERS-active structure 208 can, in various examples, be formed by any structure or grouping of structures that is conducive to enhancement of a Raman signal. For example these structures can be nearly any form of closely spaced metal nanostructures such as nanoparticles or nanopillars. These structures can be formed using solution processing techniques such as printing, dip coating as well as more deterministic approaches such as nanoimprinting where closely spaced nanostructure are formed in an embossing resin using a stamp and then coated with metal. By way of example, FIG. 2 shows a plurality of SERS-active structures 208 to be positioned in groupings of three. However, the present disclosure is not limited to such numbers and/or positioning of the plurality of SERS-active structures 208. That is, the plurality of SERS-active structures 208 can include groups of any number that is two or more that are capable of providing an enhanced Raman signal.

As described in the present disclosure, a Raman-active material 209 can, in various examples, be formed with a variety of SERS-active metal-containing materials such gold, silver, copper, platinum, iridium, gallium, lead, and/or mixtures thereof. Further, as described herein, a Raman-active metal-containing material is formed in any desired pattern on and/or at least partially within one or more surfaces of each of the plurality of SERS-active structures 208 to provide an enhanced Raman signal sensing functionality (e.g., exposing a material of interest present in the solution, which is associated with the Raman-active metal-containing material, to spectroscopy).

Figure 3A:
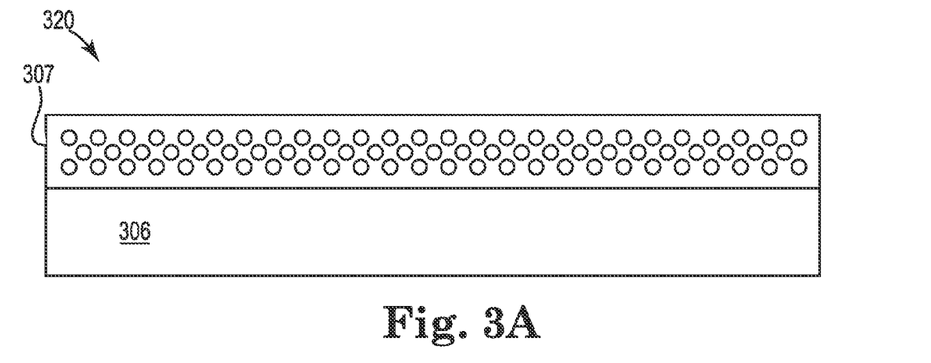
FIGS. 3A-3C illustrate an example of forming a portion of a SERS apparatus according to the present disclosure.
Figure 3B:
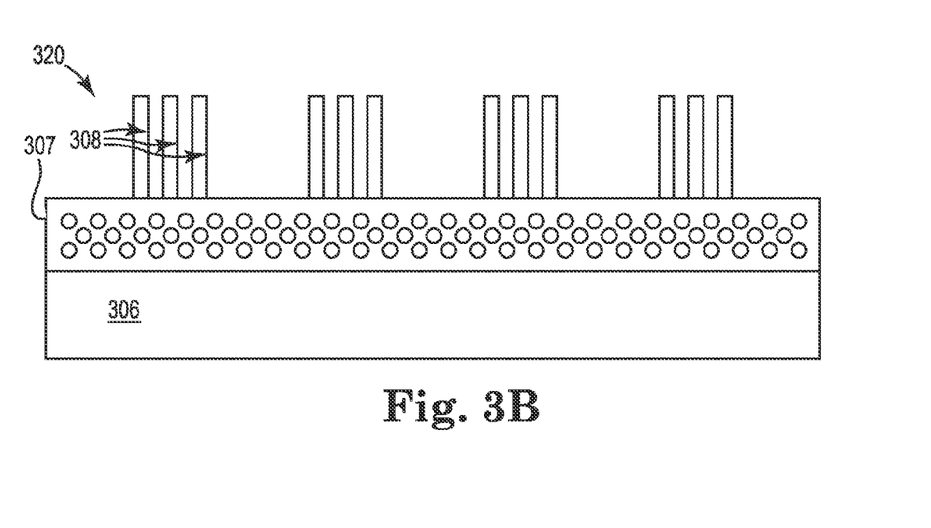
Figure 3C:
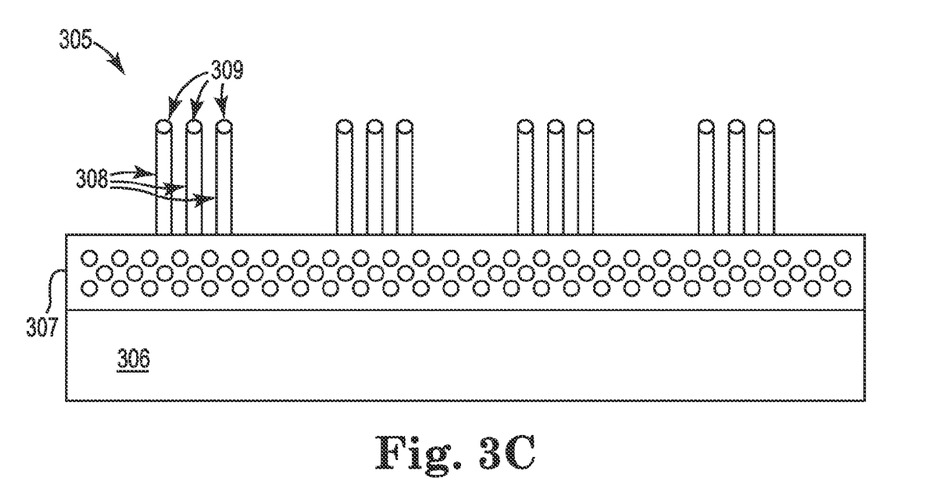

FIGS. 3A-3C illustrate an example of forming a portion of a SERS apparatus 320 according to the present disclosure. FIG. 3A illustrates forming the nanoporous material 307 on the upper surface of the substrate 306. FIG. 38 illustrates forming the plurality of SERS-active structures 308 on an upper surface of the nanoporous material 307 located on the substrate 306. FIG. 3C illustrates applying the Raman-active metal-containing material 309, where the Raman-active metal-containing material 309 is exposed on at least one surface of each of the plurality SER-active structures 308.

As described herein, the plurality of SERS-active structures 308 may be fabricated using techniques such as embossing, lamination, and/or nanoparticle printing techniques. As described herein, embossing includes forming the plurality of SERS-active structures 308 by applying mechanical pressure and/or heat, for example, to a metal sheet containing the plurality of SERS-active structures 308, and, in some examples, with an embossing resin, which is then positioned on the upper surface of the nanoporous material 307 located on the upper surface of the substrate 306. This results in the plurality of SERS-active structures 308 and embossing resin, in the instances when embossing resin is utilized, to both be embossed (e.g., affixed to protrude) on the upper surface of the nanoporous material 307. In some examples, the embossing resin is, at least partially, removed to expose at least part of the nanoporous material 307. The at least partial removal of the embossing resin can be accomplished through a variety of means (e.g., plasma etching, among others).

As described herein, lamination includes forming the plurality of SERS-active structures 308 by applying one or more sacrificial layers to the plurality of SERS-active structures 308 prior to using mechanical force and/or heat to adhere the plurality of SERS-active structures 308 to the nanoporous material 307 located on the upper surface of the substrate 306. In some examples, the plurality of SERS-active structures 308 can be nanopillars, where a first sacrificial layer is attached to the tops of the plurality of nanopillars whose bottoms are subsequently laminated to the upper surface of the nanoporous material 307, in other examples, a second sacrificial layer is laminated to the bottoms of the plurality of nanopillars. Once adhered, at least a portion of the first and/or second sacrificial layers is removed to, at least partially, expose the nanoporous material 307 beneath. The at least partial removal of the first and/or second sacrificial layers can be accomplished through a variety of means (e.g., plasma etching, among others).

In some examples, forming the plurality of SERS-active structures 308 can by accomplished by, for example, printing nanoparticles on the upper surface of the nanoporous material 307 located on the upper surface of the substrate 306. Printing methods can include use of electrophotographic and/or ink jet imaging devices, among others.

Figure 4:
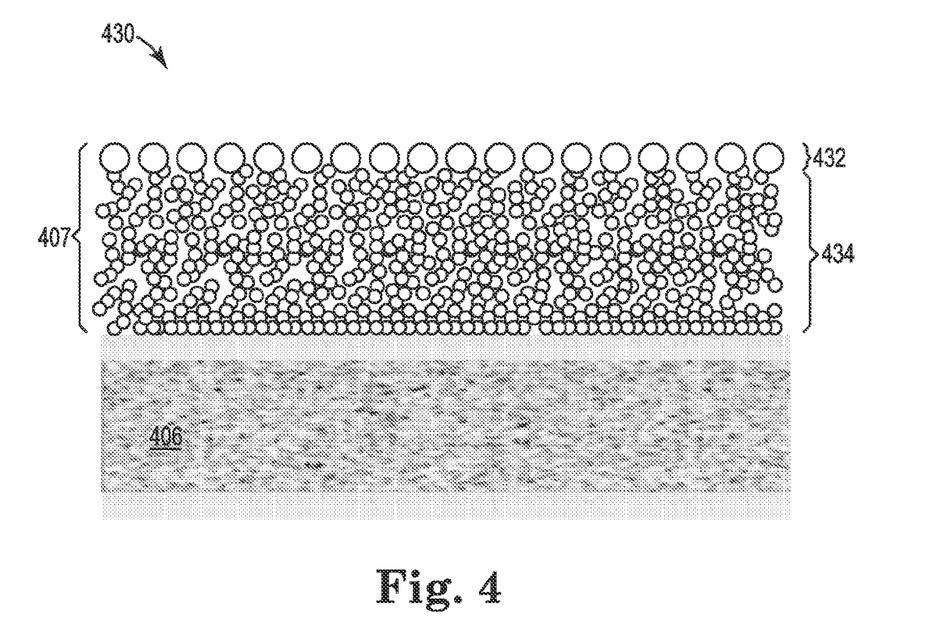
FIG. 4 illustrates an example of a SERS apparatus with a nanoporous material formed from multiple layers according to the present disclosure.

FIG. 4 illustrates an example of the SERS apparatus 430 with nanoporous material 407 formed from multiple layers according to the present disclosure. Examples disclosed herein provide properties of nanoporous material 407 that contains multiple layers exhibiting improved capillary force in a cost effective manner. FIG. 4 shows the nanoporous material 407 having a nanoporous absorbing layer 434 located on an upper surface of the substrate 406. FIG. 4 also shows a nanoporous surface layer 432 located on the upper surface of the nanoporous absorbing layer 434. In some examples, the nanoporous absorbing layer 434 can be several times thicker than the nanoporous surface layer 432. In some examples, the nanoporous surface layer 432 can have a thickness in a range of from substantially 0.1 µm to substantially 50 µm, and the nanoporous absorbing layer 434, can have a thickness in a range of from substantially 2 µm to substantially 50 µm.

As described herein, the nanoporous surface layer is one or more layers applied over the nanoporous absorbing layer. In various examples, the nanoporous surface layer can be a nanoporous layer having median pore diameters that are larger and/or smaller than the median pore diameter of the particles that form the nanoporous absorbing material located on the upper surface of the substrate surface. In some examples, the nanoporous surface layer can be a nanoporous layer having a median pore diameter in the range of about 3 nanometers (nm) to about 300 nm. In some examples, the nanoporous surface layer can be a nanoporous layer having median pore diameter in the range of about 3 nm to about 20 nm. Without being linked by any theory, it is behaved that high structural uniformity of the nanoporous surface layer helps to improve performance of the SERS structures by creating higher capillary pressure forces. In some examples, the coat weight of the nanoporous surface layer can be from about 0.1 g/m² to about 2 g/m² and, in some examples, the coat weight of the nanoporous surface layer can be from about 0.25 g/m² to about 1.0 g/m².

The nanoporous surface layer can contain inorganic colloidal particles, for example, colloidal particulates of metal oxides and semi-metal oxides or colloidal silica particles and water-soluble binders. The median particle size, as measured by diameter, of the inorganic colloidal particles present in the nanoporous surface layer can, for example, be from about 5 nm to about 300 nm. In some examples, the median particle size can be from about 20 nm to about 100 nm. The inorganic colloidal particles suitable for the nanoporous surface layer can be discrete, single particles (e.g., they are not aggregates of primary particles). Inorganic colloidal particles can be selected from the group consisting of silica, aluminum oxides, clay, kaolin, calcium carbonate, talc, titanium dioxide, and/or zeolites, among others. In some examples, inorganic colloidal particles present in the nanoporous surface layer can be inorganic oxide colloidal particles such as colloidal silica, aluminum oxides (e.g., boehmites), and mixtures of these. In some examples, the nanoporous surface layer contains spherical colloidal silicas with particle size ranging from about 30 nm to about 80 nm. In some examples, the absorbing capacity of the nanoporous surface layer can be less than about 0.2 milliliters/gram (ml/g).

The nanoporous surface layer can contain various binders. Such binders can be polyvinylalcohol or a copolymer of vinylpyrrolidone. The copolymer of vinylpyrrolidone can include various other copolymerized monomers, such as methyl acrylates, methyl methacrylate, ethyl acrylate, hydroxyethyl acrylate, hydroxyethyl methacrylate, ethylene, vinylacetates, vinylimidazole, vinylpyridine, vinylcaprolactams, methyl vinylether, maleic anhydride, vinylamides, vinylchloride, vinylidene chloride, dimethylaminoethyl methacrylate, acrylamide, methacrylamide, acrylonitrile, styrene, acrylic acid, sodium vinylsulfonate, vinylpropionate, and/or methyl vinylketone, etc. The nanoporous surface layer can contain colloidal silica and greater than 5 weight percent (wt %) of polyvinylalcohol. In some examples, binders can be present in the layer at from about 0 wt % to about 15 wt %. In some examples, the wt % of binder, based on the total dry weight of inorganic colloidal particles, can range from about 5 wt % to about 12 wt %.

As described herein, a nanoporous absorbing layer can be a layer with an absorption capacity (e.g., porosity) ranging from about 0.6 ml/g to about 1.2 ml/g. The median particle size, as measured by diameter, of the particles present in the nanoporous absorbing layer can, for example, be from about 5 nm to about 300 nm. In some examples, the nanoporous absorbing layer can be a nanoporous layer having a median pore diameter in the range of about 3 nm to about 300 nm. The nanoporous absorbing layer can have a coat weight in the range of about 10 g/m² to about 40 g/m². In other examples, the nanoporous absorbing layer can have a coat weight in the range of about 15 g/m² to about 30 g/m². The nanoporous absorbing layer can include inorganic pigments (e.g., in particulate form).

The nanoporous absorbing layer can include inorganic particulates. Suitable inorganic particulates include metal oxides and/or semi-metal oxide particulates. The inorganic semi-metal oxide or metal oxide particulates may be independently selected from silica, alumina, boehmite, silicates (such as aluminum silicate, magnesium silicate, and the like), titania, zirconia, calcium carbonate, clays, or combinations thereof.). The inorganic particulates can be fumed alumina. In some examples, the inorganic particulates can be fumed silica (e.g., modified or unmodified). Thus, the inorganic particulates can include any number of inorganic oxide groups including, but not limited to silica and/or alumina, including those treated with silane coupling agents containing functional groups or other agents such as aluminum chlorohydrate (ACH) and those having oxide/hydroxide. If silica is used, it can be selected from the following group of commercially available fumed silicas: Cab-O-Sil®LM-150, Cab-O-Sil®M-5, Cab-O-Sil®MS-55, Cab-O-Sil®MS-75D, Cab-O-Sil®H-5, Cab-O-Sil®HS-5, Cab-O-Sil®EH-5, Aerosil®150, Aerosil®200, Aerosil®300, Aerosil®350, and/or Aerosil®400.

In some examples, an aggregate size of the fumed silica can be from approximately 50 to 300 nm in size. In some other examples, the fumed silica can be from approximately 100 to 250 nm in size. An Brunauer-Emmett-Teller (BET) surface area of the fumed silica can be from approximately 100 to 400 square meters per gram. In some examples, the fumed silica can have a BET surface area from approximately 150 to 300 square meters per gram ($m^2/g$). The inorganic particulates can be alumina (e.g., modified or unmodified). In some examples, the alumina coating can comprise pseudo-boehmite, which is aluminum oxide/hydroxide ($Al_2O_3 \times n\ H_2O$ where n is from 1 to 1.5). Commercially available alumina particles can also be used, including, but not limited to, Sasol Disperal®/HP10, Disperal®HP14, boehmite, Cabot Cab-OSperse® PG003 and/or CabotSpectrAl®81 fumed alumina.

In some examples, the nanoporous absorbing layer can contain fumed silica and/or fumed aluminas, which are aggregates of primary particles. In some examples, the nanoporous absorbing layer contains fumed silica or fumed aluminas that have a median particle size ranging from about 10 nm to about 250 nm. The amount of inorganic pigment may be from about 30 to 90 by weight (wt %) based on the total weight of the nanoporous absorbing layer, or, in some other examples, from about 60 wt % to about 80 wt %.

A binder can be added to the nanoporous absorbing layer to bind the particulates together. In some examples, an amount of binder is added that provides a balance between binding strength and maintaining particulate surface voids and interparticle spaces for allowing liquid to be absorbed. The binders can, in some examples, be selected from polymeric binders. In some examples, the binders can be water-soluble polymers and polymer latexes. Examples of binders include: polyvinyl alcohols and water-soluble copolymers thereof, (e.g., copolymers of polyvinyl alcohol and poly(ethylene oxide) or copolymers of polyvinyl alcohol and polyvinylamine; cationic polyvinyl alcohols; aceto-acetylated polyvinyl alcohols; polyvinyl acetates; polyvinyl pyrrolidones including copolymers of polyvinyl pyrrolidone and polyvinyl acetate; gelatin; silyl-modified polyvinyl alcohol; styrene-butadiene copolymer; acrylic polymer latexes; ethylene-vinyl acetate copolymers; polyurethane resin; polyester resin; and combination thereof. In some examples, the binder is polyvinylalcohol with a percentage hydrolysis between 80% to 90% with 4 wt. % aqueous solution having viscosity equal or higher than 30 Centipoises at 25° C. Examples of binders include Poval®235, Mowiol®56-88, Mowiol®40-88). In some examples, the binder may be present in an amount representing about 5 wt % to about 30 wt % by total weight of the nanoporous absorbing layer.

A nanoporous layer can contain organic particles, for example, block copolymers. By way of example and not by way of limitation, block copolymers can include two or more of poly(ethylene oxide)-b-poly(styrene) (PEO-b-PS), poly(styrene)-b-poly(methyl methacrylate)(PS-b-PMMA), polycarbonate, polyethylene, polypropylene, polyisobutylene, polybutadiene, polyisoprene, polyacrylonitrile, poly(vinyl alcohol), poly(vinyl acetate), poly(vinyl chloride), poly(vinylidene fluoride), poly(tetrafluoroethylene), poly(vinyl butyral), poly(methyl acrylate), poly(ethylene oxide), poly(phenylene oxide), poly(ethylene terephthalate), poly(hexamethylene adipamide), trimethylene terephthalate, and/or butyl acrylate. In some examples, the block copolymers can contain plasticizers, fillers, and/or dyes. The block copolymers can phase separate. This separation can create distinct chemical blocks (e.g., formed from PMMA, PEO, and PS) in the nanoporous layer.

As described herein, lithography can be utilized for at least partial removal of the nanoporous material 307 located on the upper surface of the substrate 306. The at least partial removal of the nanoporous material (e.g., distinct chemical blocks such as PMMA, among others) can be accomplished through a variety of means (e.g., ultraviolet (UV) degradation, reactive ion etching, and/or plasma etching, among others). In some examples, such films can serve as lithographic masks for reactive ion etching using an etchant (e.g., trifluoromethane ($CHF_3$), among others). The lithographic masks can, in some examples, be transferred to the substrate 306. In some further examples, the lithographic masks etched with reactive ions can be plasma etched (e.g., with $O_2$ plasma) to remove at least some of a remaining nanoporous material.

An example of a technique for formation of the nanoporous material as described herein is detailed as follows. Nanoporous coated substrates can be produced by a single pass (e.g., wet-on-wet) coating using a curtain coater. The nanoporous absorbing layer and the optional nanoporous surface layer can be applied onto a base substrate. The nanoporous absorbing layer can be applied first to a front side of the paper with a roller coater. When present, the nanoporous surface layer can be coated on the top of the nanoporous absorbing layer. The coat weight of the nanoporous absorbing layer can, for example, be from about 2 $g/m^2$ to about 40 $g/m^2$ and the coat weight of the nanoporous surface layer can, for example, be from about 0.1 $g/m^2$ to about 2 $g/m^2$.

Formulations of examples of different coating layers are shown in Table 1 below. Table 1 describes composition of two example versions of the nanoporous coated substrate. Version A has the optional nanoporous surface layer, while Version B omits the nanoporous surface layer. Numbers in Table 1 represent the weight parts of each component present in each layer.

TABLE 1

| Layer | Ingredients | Version A | Version B |
|---|---|---|---|
| Nanoporous Surface Layer | Disperal ®HP-14 | 75 | — |
|  | Cartacoat ®K30 3C | 25 | — |
|  | PVA 2 | 11 | — |
| Coat weight |  | 0.5 g/m² | — |
| Nanoporous absorbing layer | Treated Silica | 100 | 100 |
|  | PVA 1 | 21 | 21 |
|  | Boric Acid | 2.5 | 2.5 |
|  | Silwet ®L-7600 | 0.5 | 0.5 |
|  | Glycerol | 1.5 | 1.5 |
|  | Zonyl ®FSN | 0.1 | 0.1 |
| Coat weight |  | 28 g/m² | 28 g/m² |

As shown in Table 1, the treated silica can be Cab-O-Sil®MS-55 treated with aluminum chlorohydrate and Silquest®A-1110. PVA 1 is Poval®235. PVA 2 is Mowiol® 40-88. Zonyl®FSN is a fluorosurfactant. Cartacoat®K303C is a cationic colloidal silica. Disperal®HP-14 is boehmites. Silwet®L-7600 is a surfactant.

Figure 5A:
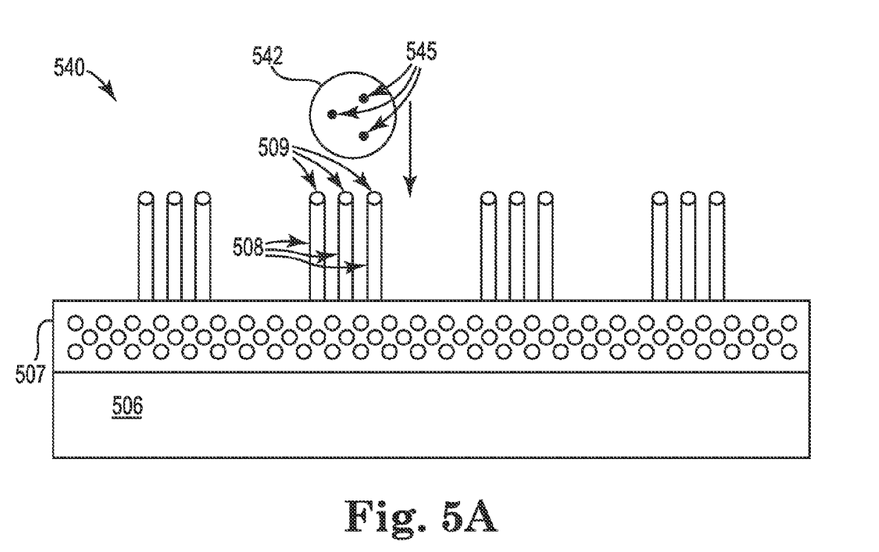
FIGS. 5A-5B illustrate an example of operating a SERS apparatus according to the present disclosure.
Figure 5B:
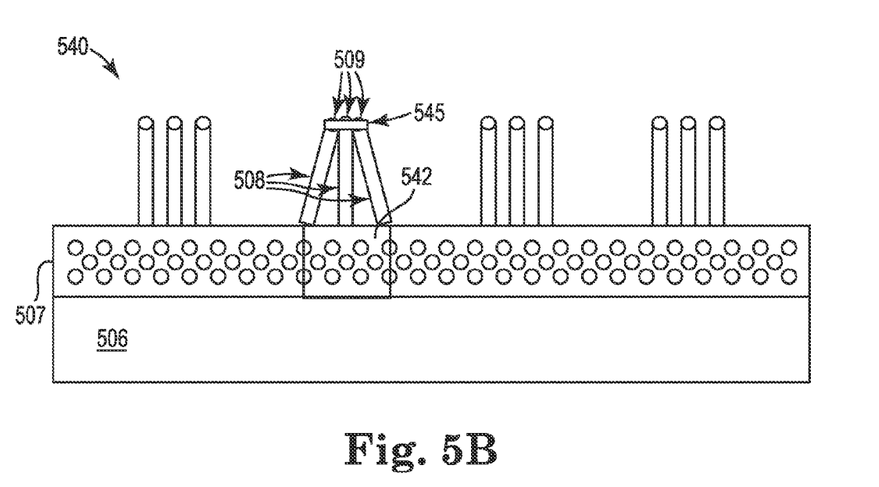

FIGS. 5A-5B illustrate an example of operating a SERS apparatus 540 according to the present disclosure. FIG. 5A illustrates operating the SERS apparatus 540 by applying a solution 542 containing a material of interest 545 to a number of SERS-active structures 508 on an upper surface of a nanoporous material 507 located on the upper surface of a substrate 506, where the number of SERS-active structures 508, include a Raman-active metal-containing material 509 exposed on a surface of each of the number of the SERS-active structures 508.

FIG. 5B illustrates drawing the solution 542 into the plurality of SERS-active structures 508 by capillary force applied by the nanoporous material 507 to absorb the solution into the nanoporous material 507. In some examples, the capillary force is applied entirely in a direction normal to the nanoporous material and/or the substrate (e.g., perpendicular). Further, examples of the plurality of SERS-active structures 508 in the present disclosure include, but are not limited to, arrays of nanoparticles, nanopillars, and/or combinations thereof.

FIG. 5B illustrates exposing the material of interest 545 present in the solution 542, which is associated with the Raman-active metal-containing material 509, to spectroscopy. In some examples, as illustrated in FIG. 5B, operating the SERS apparatus 540 can include collapsing a plurality of nanopillars at least partially effectuated by the capillary force applied by the nanoporous material 506 to expose the material of interest 545 to the spectroscopy.

Figure 6A:
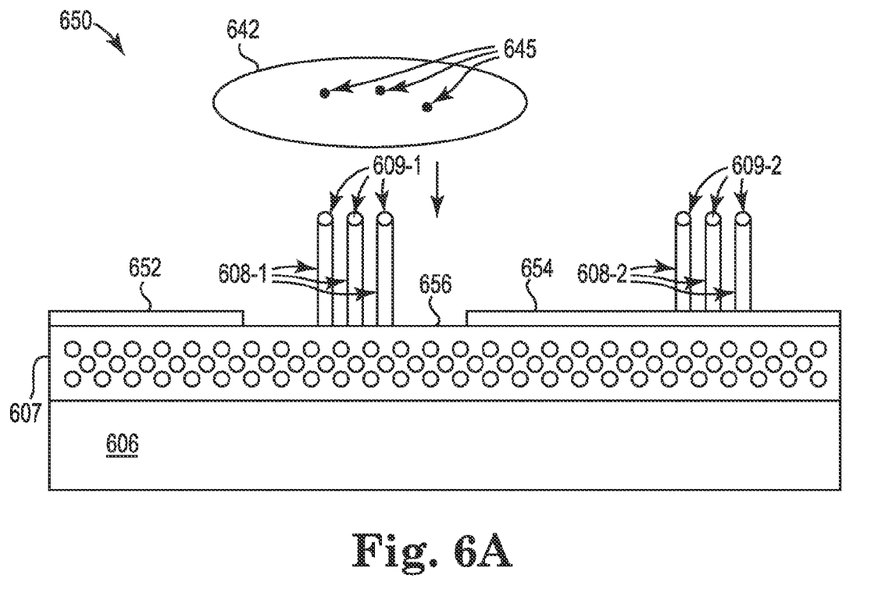
FIGS. 6A-6B illustrate an example of forming and operating a SERS apparatus according to the present disclosure.
Figure 6B:
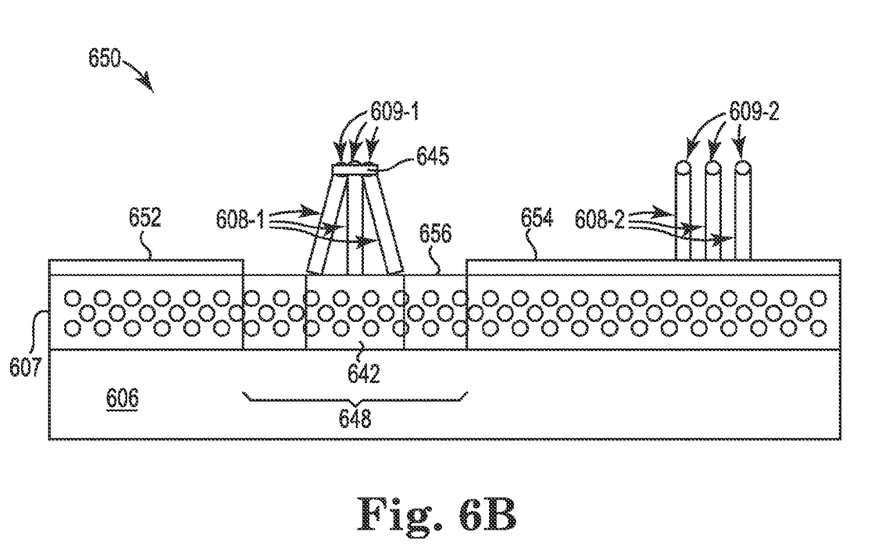

FIGS. 6A-6B illustrate an example of forming and operating a SERS apparatus 650 according to the present disclosure. FIG. 6A illustrates forming, at least partially, an exposed area 656 on what is otherwise a covered area 652, 654 of the upper surface of a nanoporous material 607 located on the upper surface of a substrate 606. In some examples, the upper surface of the nanoporous material 607 can have a plurality of the exposed areas 656 and covered areas 652, 654. In some examples, as shown in FIG. 6A, the exposed area of the nanoporous material 607 can have a plurality of SERS-active structures 608-1 with the Raman-active metal-containing materials 609-1 on the upper surface thereof. In some examples, as shown by FIG. 6A, the covered sections 652, 654 of the nanoporous material 607 can have a plurality of SERS-active structures 608-2 with a Raman-active metal-containing material 609-2 on the upper surface thereof.

FIG. 6B illustrates, in examples where the SERS-active structures 608-1 are nanopillars, operating the SERS apparatus 650 by collapsing a plurality of nanopillars 608-1 at least partially effectuated by capillary force, applied by the partially exposed area 656 of the nanoporous material 607, to expose the material of interest 645 to the spectroscopy. In some examples, the nanoporous material 607, and the substrate 606 can both absorb excess solution 642.

In some examples, the capillary force being applied normal to the nanoporous material and/or the substrate (e.g., perpendicular) can result in the solution being confined to directly under the SERS-active structures, as shown at 642. In some examples, for example when there is a large drop of solution 642 containing the material of interest 645, as shown in FIG. 6A, the solution can be confined to the exposed area 648 of the nanoporous absorbing layer by adjacent areas 652, 654 being covered.

The present disclosure describes examples of SERS apparatuses employing a directional capillary force contributing to the reliable utilization of SERS-active structures for enhancement of a Raman signal. Additionally, the capillary force can be localized in a manner to produce a variety of SERS-active structure shapes, patterns, and configurations. These SERS structures can be used in a variety of applications (e.g., detection of odorants, solvents, and/or solutes, such as in detection and identification of explosives, contraband, drug discovery, biological outgas, medical applications, toxic industrial chemicals, agricultural organics, fugitive emissions, DNA sequence detection, intracellular studies, among other applications).

The present disclosure includes apparatuses and methods for implementing SERS-active structures on a nanoporous coated substrate. SERS apparatuses can be used for the applications described in the present disclosure, although the SERS apparatuses are not limited to such applications.

It is to be understood that the above description has been made in an illustrative fashion and not a restrictive one. Although specific examples for devices and methods have been illustrated and described herein, other equivalent component arrangements and/or SERS-active structures can be substituted for the specific examples shown herein.

What is claimed:

1. A surface enhanced Raman spectroscopy (SERS) apparatus, comprising:
a nanoporous material on an upper surface of a substrate;
a plurality of SERS-active structures on an upper surface of the nanoporous material; and
an exposed Raman-active material disposed on or at least partially within a surface of each of the SERS-active structures;
wherein the nanoporous material comprises a nanoporous surface layer, with a median pore diameter in a range of from substantially 3 nanometers (nm) to substantially 300 nm, and a nanoporous absorbing layer, with a median pore diameter in a range of from substantially 3 nm to substantially 300 nm.

2. The apparatus of claim 1, wherein the nanoporous material has a thickness in a range of from substantially 2 microns (µm) to substantially 50 µm.

3. The apparatus of claim 1, wherein the nanoporous material comprises a nanoporous surface layer, with a thickness in a range of from substantially 0.1 µm to substantially 50 µm, and a nanoporous absorbing layer, with a thickness in a range of from substantially 2 µm to substantially 50 µm.

4. The apparatus of claim 1, wherein the nanoporous material comprises inorganic colloidal particles or organic block copolymers.

5. The apparatus of claim 1, wherein the plurality of SERS-active structures comprises arrays of nanoparticles, nanopillars, and/or combinations thereof.

6. The apparatus of claim 1, wherein the Raman active material comprises metals selected from the group consisting of gold, silver, copper, platinum, iridium, gallium, lithium, lead, and mixtures thereof; and wherein the Raman-active material is on an end, distal to the upper surface of the nanoporous material, of each of the SERS-active structures.

7. The apparatus of claim 1, wherein the substrate is selected from the group consisting of cellulosic or synthetic paper, cardboard, polymeric film, fabric, and cloth.

8. The apparatus of claim 4, wherein the nanoporous material comprises the inorganic colloidal particles, and wherein the inorganic colloidal particles are selected from the group consisting of silica, aluminum oxides, clay, kaolin, calcium carbonate, talc, titanium dioxide, zeolites, and combinations thereof.

9. A surface enhanced Raman spectroscopy (SERS) apparatus, comprising:

a nanoporous material on an upper surface of a substrate;
a plurality of SERS-active structures on an upper surface of the nanoporous material; and
an exposed Raman-active material disposed on or at least partially within a surface of each of the SERS-active structures;
wherein the nanoporous material comprises a nanoporous surface layer, with a median particle diameter in a range of from substantially 5 nanometers (nm) to substantially 300 nm, and a nanoporous absorbing layer, with a median particle diameter in a range of from substantially 5 nm to substantially 300 nm.

10. The apparatus of claim 9, wherein the nanoporous material comprises a nanoporous surface layer, with a thickness in a range of from substantially 0.1 μm to substantially 50 μm, and a nanoporous absorbing layer, with a thickness in a range of from substantially 2 μm to substantially 50 μm.

11. A method of forming a surface enhanced Raman spectroscopy (SERS) apparatus, comprising:
forming a nanoporous material on an upper surface of a substrate;
forming a plurality of SERS-active structures on an upper surface of the nanoporous material; and
applying a Raman-active metal-containing material to the plurality of SERS-active structures, wherein the Raman-active metal-containing material is exposed on a surface of each of the plurality of SERS-active structures;
wherein:
the nanoporous material comprises a nanoporous surface layer, with a median pore diameter in a range of from substantially 3 nanometers (nm) to substantially 300 nm, and a nanoporous absorbing layer, with a median pore diameter in a range of from substantially 3 nm to substantially 300 nm; or
the nanoporous material comprises a nanoporous surface layer, with a median particle diameter in a range of from substantially 5 nanometers (nm) to substantially 300 nm, and a nanoporous absorbing layer, with a median particle diameter in a range of from substantially 5 nm to substantially 300 nm.

12. The method of claim 11, wherein forming the nanoporous material comprises applying the nanoporous material to the upper surface of the substrate by single-pass curtain coating.

13. The method of claim 11, wherein forming the plurality of SERS-active structures comprises forming a plurality of nanopillars.

14. The method of claim 13, wherein forming the plurality of nanopillars comprises attaching tops of the plurality of nanopillars to a sacrificial material, laminating bottoms of the plurality of nanopillars to the upper surface of the nanoporous material, and removing the sacrificial material.

15. The method of claim 13, wherein forming the nanoporous material further comprises forming at least one partially exposed area on an otherwise covered area of the upper surface of the nanoporous material.

16. A method of operating a surface enhanced Raman spectroscopy (SERS) apparatus, comprising:
applying a solution to a number of SERS-active structures on an upper surface of a nanoporous material disposed on an upper surface of a substrate, wherein the number of SERS-active structures comprises an exposed Raman-active metal-containing material disposed on or at least partially within a surface of each of the number of SERS-active structures;
drawing the solution into the SERS-active structures by capillary force applied by the nanoporous material to absorb the solution into the nanoporous material; and
exposing a material of interest present in the solution that is associated with the Raman-active metal-containing material to spectroscopy;
wherein:
the nanoporous material comprises a nanoporous surface layer, with a median pore diameter in a range of from substantially 3 nanometers (nm) to substantially 300 nm, and a nanoporous absorbing layer, with a median pore diameter in a range of from substantially 3 nm to substantially 300 nm; or
the nanoporous material comprises a nanoporous surface layer, with a median particle diameter in a range of from substantially 5 nanometers (nm) to substantially 300 nm, and a nanoporous absorbing layer, with a median particle diameter in a range of from substantially 5 nm to substantially 300 nm.

17. The method of claim 16, wherein the SERS-active structures are a plurality of nanopillars, and wherein the method further comprises collapsing a plurality of nanopillars, at least partially effectuated by the capillary force applied by the nanoporous material, to expose the material of interest to the spectroscopy.

18. A surface enhanced Raman spectroscopy (SERS) apparatus, comprising:
a nanoporous material on an upper surface of a substrate;
a plurality of SERS-active structures on an upper surface of the nanoporous material; and
an exposed Raman-active material disposed on or at least partially within a surface of each of the SERS-active structures;
wherein the nanoporous material comprises organic block copolymers, and wherein the organic block copolymers include two or more compounds selected from the group consisting of poly(ethylene oxide)-b-poly(styrene) (PEO-b-PS), poly(styrene)-b-poly(methyl methacrylate)(PS-b-PMMA), polycarbonate, polyethylene, polypropylene, polyisobutylene, polybutadiene, polyisoprene, polyacrylonitrile, poly(vinyl alcohol), poly (vinyl acetate), poly(vinyl chloride), poly(vinylidene fluoride), poly(tetrafluoroethylene), poly(vinyl butyral), poly(methyl acrylate), poly(ethylene oxide), poly(phenylene oxide), poly(ethylene terephthalate), poly(hexamethylene adipamide), trimethylene terephthalate, and butyl acrylate.

19. A surface enhanced Raman spectroscopy (SERS) apparatus, consisting of:
a substrate;
a nanoporous material, consisting of:
a nanoporous absorbing layer disposed on an upper surface of the substrate, the nanoporous absorbing layer being inorganic particulates selected from the group consisting of silica, alumina, boehmite, aluminum silicate, magnesium silicate, titania, zirconia, calcium carbonate, clays, and combinations thereof, the nanoporous absorbing layer optionally including a binder; and
a nanoporous surface layer disposed on an upper surface of the nanoporous absorbing layer, the nanoporous surface layer being inorganic colloidal particles selected from the group consisting of silica, aluminum oxides, clay, kaolin, calcium carbonate, talc, titanium dioxide, zeolites, and combinations thereof, the nanoporous surface layer optionally including a binder;

a plurality of SERS-active structures on an upper surface of the nanoporous surface layer; and an exposed Raman-active material disposed on or at least partially within a surface of each of the SERS-active structures.

20. The apparatus of claim 19 wherein the SERS-active structures are a plurality of nanopillars, and wherein the substrate is selected from the group consisting of cellulosic or synthetic paper, cardboard, polymeric film, fabric, and cloth.

21. The apparatus of claim 19, wherein the nanoporous surface layer has a median pore diameter in a range of from substantially 3 nanometers (nm) to substantially 300 nm, and wherein the nanoporous absorbing layer has a median pore diameter in a range of from substantially 3 nm to substantially 300 nm.

* * * * *

UNITED STATES PATENT AND TRADEMARK OFFICE
CERTIFICATE OF CORRECTION

PATENT NO. : 9,574,990 B2
APPLICATION NO. : 14/377708
DATED : February 21, 2017
INVENTOR(S) : Devin Alexander Mourey et al.

Page 1 of 1

It is certified that error appears in the above-identified patent and that said Letters Patent is hereby corrected as shown below:

In the Claims

In Column 10, Line 51, in Claim 6, delete "Raman active" and insert -- Raman-active --, therefor.

Signed and Sealed this
Twenty-third Day of May, 2017

Michelle K. Lee
*Director of the United States Patent and Trademark Office*